United States Patent [19]

Burstein et al.

[11] 4,408,359
[45] Oct. 11, 1983

[54] HIP JOINT PROSTHESIS

[75] Inventors: Albert H. Burstein, Greenwich, Conn.; Donald L. Bartel, Freeville, N.Y.

[73] Assignee: New York Society for the Relief of the Ruptured and Crippled, Maintaining the Hospital for Special Surgery, New York, N.Y.

[21] Appl. No.: 251,883

[22] Filed: Apr. 7, 1981

[51] Int. Cl.³ .............................................. A61F 1/04
[52] U.S. Cl. .................................. 3/1.912; 128/92 C
[58] Field of Search ........................... 3/1.912, 1.913; 128/92 C, 92 CA

[56] References Cited

U.S. PATENT DOCUMENTS

| | | | |
|---|---|---|---|
| 4,040,129 | 8/1977 | Steinemann et al. | 128/92 C |
| 4,101,985 | 7/1978 | Baumann et al. | 3/1.913 |
| 4,141,088 | 2/1979 | Treace et al. | 128/92 CA |

FOREIGN PATENT DOCUMENTS

| | | | |
|---|---|---|---|
| 2324865 | 11/1974 | Fed. Rep. of Germany | 3/1.913 |
| 2331728 | 1/1975 | Fed. Rep. of Germany | 3/1.913 |
| 2842847 | 4/1980 | Fed. Rep. of Germany | 3/1.913 |
| 27160 | 4/1981 | Fed. Rep. of Germany | 3/1.913 |
| 1046516 | 7/1953 | France | 128/92 CA |

OTHER PUBLICATIONS

Publication, 1974 of Jan., to Zimmer, "Hip Prosthesis Size Definition Chart".

Primary Examiner—Richard J. Apley
Assistant Examiner—David G. Isabella
Attorney, Agent, or Firm—Brumbaugh, Graves, Donohue & Raymond

[57] ABSTRACT

A total hip joint prosthesis has a ball, replacing the ball of the hip joint ball and socket, affixed to the femur by a stem. Stem stress is reduced by providing a rounded cross-section of the stem truncated along the lateral side in the critical section subject to greatest cyclic loading. The stem is of controlled low flexibility so that when the bone cement and stem composite structure is in place, the bone is subject to a maximum percent of normal stress from bending moments. By virtue of the truncated shape and its size relative to the bone cavity, stress in the stem is minimized when the stem alone carries the load.

6 Claims, 9 Drawing Figures

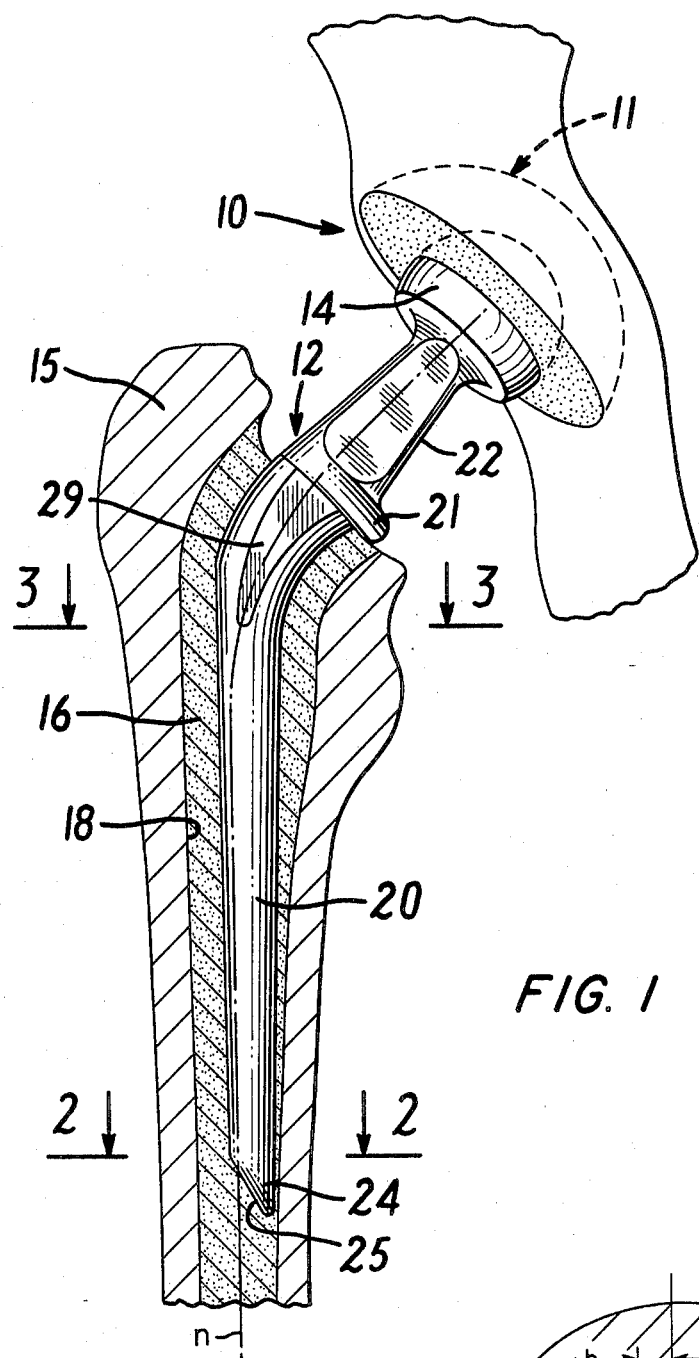
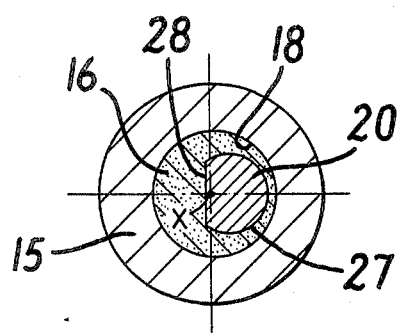
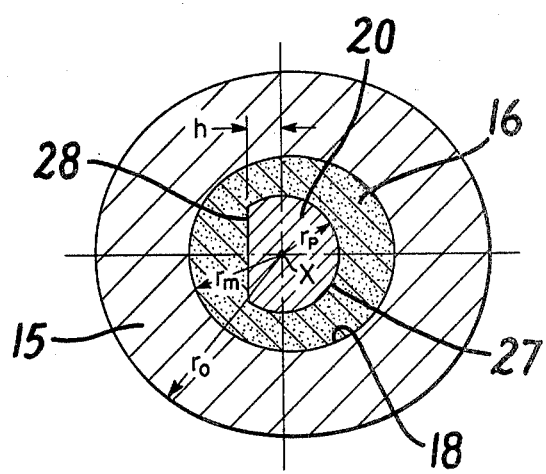
FIG. 1
FIG. 2
FIG. 3

$\tilde{h} = h/r_p$

HIP JOINT PROSTHESIS

BACKGROUND OF THE INVENTION

This invention relates to a hip joint prosthesis having an improved femoral fixation stem.

The femoral ball of a total hip joint prosthesis is affixed to the femur by a fixation stem that is received in the medullary cavity of the femur and held in place by a cement. Over a period of years the femur and, of course, the fixation stem are subjected to several tens of thousands of load cycles consisting primarily of compression and bending loads. Reducing the load during such cyclic loading of any structural member is a high priority objective in the design of such a member. Generally, stresses occurring during these load cycles are greatest in the middle third of the stem. There, tension due to flexure is greatest.

It might seem that the problem of reducing stress could be solved quite easily by providing a stem capable of carrying a higher load with less flexure based on the choice of materials used for the stem and the size and geometry. This approach, however, is unsuccessful. When the femoral fixation stem is in place in the medullary cavity of the femur and the composite structure of bone, cement, and stem is intact, greater stiffness of the stem relative to the bone loads the stem more heavily, taking load off of the bone. Since bone remodels according to the load applied to it, reducing the load on the bone results in a decrease in the amount of bone in the composite structure. Aside from the fact that deterioration of the bone is unwanted, a potential vicious circle exists. The decreased amount of bone that results from decreased bone loading also decreases the stiffness afforded by the bone. This increases the relative stiffness of the chosen stem with respect to the diminished bone. This, in turn, further reduces the load on the bone. Hence, the apparent approach to reducing stress results in an accelerating deterioration of the composite bone, cement, and stem structure that secures the ball of the hip joint prosthesis to the upper leg.

BRIEF SUMMARY OF THE INVENTION

There is provided, in accordance with the present invention, a femoral fixation stem of a hip joint prosthesis that decreases stem stress. The stem meets three conditions or design criteria to minimize stress in the stem and maximize stress in the bone. First, stresses in the stem are minimized when the stem is part of the intact bone, cement, and stem composite structure. Second, the stresses in the stem are minimized when proximal support is reduced or lost and the stem must carry most or all of the load alone. Third, the decrease in stress in the bone as a result of the presence of the stem is minimized.

The first two conditions just described are competing. In the first case, when the composite structure is intact, since the load on the structure is shared among the components according to the relative stiffness of the components, the stem with the least cross-section will be the most lightly loaded by virtue of its greater flexibility and will, therefore, have the least stress. For the second condition, where the stem alone supports the load, the stem that is largest in cross-section will have the least stress.

By modification of the cross-sectional shape of the fixation stem, a stem has been provided that has controlled low flexibility relative to the surrounding bone such that a reduction is achieved in stress in that region of the stem where tension due to flexure is greatest. This portion of the stem is referred to herein as the "intermediate portion." In this intermediate portion a rounded cross-section truncated by a flattened lateral side gives a substantially increased cross-sectional dimension where bending loads are ordinarily greatest when the stem alone carries the load. For the intact composite structure, on the other hand, the larger dimension afforded by the truncated lateral side locates the thicker stem portion nearer the neutral axis of bending, where stresses from bending moments are least. This permits the bone at the lateral side of the femur to carry the greatest stress by virtue of the increased tension there, where the bone is most remote from the neutral axis of bending.

In short then, the femoral fixation stem according to the invention meets the three design criteria outlined above. It minimizes stem stress when the composite structure is intact. It minimizes stem stress when proximal support has been lost and the stem alone carries the load from the joint to the point of remaining support. It minimizes the decrease in bone stress when the composite structure is intact.

The cross-sectional shape of the intermediate portion can be a truncated ellipse which fills the medullary cavity in the anterior-posterior and medial directions and has a flat that truncates the ellipse on the lateral side. The elliptical cross-section best approximates the cross-sectional shape of the medullary cavity. However, a cross-sectional shape based on circular geometry is preferred by virtue of its advantages for manufacturing and implantation.

For correct location of the stem in the cavity an inclined surface at the distal end of the stem directs the stem toward the medial side of the medullary cavity as the stem is inserted through cement that fills the cavity. Upwardly, a collar at the proximal end of the stem terminates that portion of the stem that is to reside in the cavity. This collar ordinarily seats on the upper extremity of the femur. Of course, a neck section extends upward from the collar and terminates in the ball of the ball and socket joint of the total hip prosthesis.

The flexibility of the intermediate stem portion of the prosthesis is minimized consistent with the above three design criteria. The preferred material of the stem is Ti 6Al 4V (titanium alloyed with 6% aluminum and 4% vanadium). The dimensions and hence flexibility of the stem are chosen so that $\sigma_{Bcomposite}$, the stress in the bone of the femur proximate the lower stem with said lower stem cemented in place, is greater than or equal to about 0.7 $\sigma_{Balone}$, the stress in the bone of the femur absent the stem and cement, and under like load. At the same time, $\sigma_{Palone}$, the stress in the prosthesis femur fixation stem, absent support of surrounding cement and bone, is less than $S_{PF}$, the stress sufficient to eventuate in fatigue of the stem. Contributing to these improved characteristics of the particular stem of the preferred embodiment is the location of the flat that truncates the lateral side of the otherwise circular cross-section. The flat is removed from the center of the circular portion of the cross-section by a distance h. The distance h is greater than or equal to approximately 0.5 $r_p$ and less than or equal to approximately 0.7 $r_p$, where $r_p$ is the radius of the circular portion of the cross-section. In a specific preferred embodiment, h is approximately 0.65 $r_p$.

The above and further features and advantages of the invention will be better understood by reference to the following detailed description of a preferred embodiment, taken in conjunction with the accompanying drawings.

DESCRIPTION OF THE DRAWINGS

In the drawings:

FIG. 1 is a front elevational view of the embodiment as implanted.

FIG. 2 is a cross-sectional view along the line 2—2 of FIG. 1 and shows the truncated cross-section of the stem at its lower end.

FIG. 3 is a cross-sectional view along the line 3—3 of FIG. 1 and shows the truncated cross-section of the stem at an enlarged upper portion of the stem.

DESCRIPTION OF PREFERRED EMBODIMENT

Figure 4A:
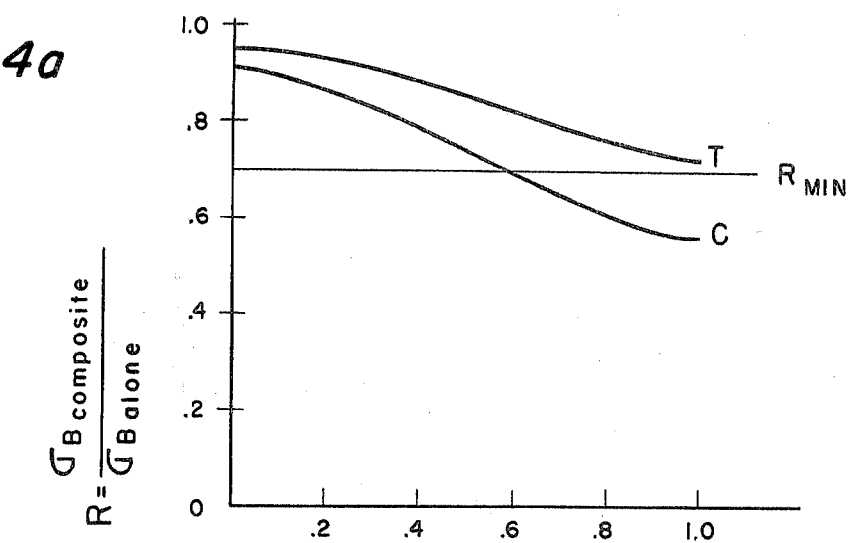
FIG. 4a is a graphical representation plotting R, the ratio of stress in the bone in the composite structure to stress in the bone alone, against $\tilde{h}$, the ratio of offset of the flat to the radius of the stem cross-section.

The prosthesis 10 includes a socket member or assembly 11 that is only schematically illustrated because its details do not form a part of the present invention. Suffice it to say, the socket member 11 can be formed in accordance with known practices in the art.

The femoral member 12, which provides the ball 14 of the hip joint prosthesis is secured to the femur 15 by cement 16 filling the medullary cavity 18 and fixing a femoral fixation stem 20 in place within the medullary cavity. A collar 21 defines the upper end of the stem 20 and resides at the upper end of the femur and its medullary cavity to locate the stem 20 at the desired depth in the cement-filled cavity. A neck section 22 of the femoral member 12 extends superiorly and medially from the collar to locate the ball 14 relative to the femur 15 and secure the ball to the stem 20.

At the tip 24 or distal end portion of the stem 20 is a surface 25 that slopes downwardly and medially and helps guide the tip 24 towards the medial side of the cavity 18 as the stem 20 is inserted through the still-to-set cement 16. The tendency, then, is for the stem 20 to locate, during insertion, closer to the medial side of the cavity, as desired.

The cross-section of the stem 20 at all locations along its length between the section lines 2—2 and 3—3 (namely, the portion of the stem that is referred to herein as the intermediate portion) is circular about a major part of its periphery 27 and truncated by a flat 28. The stem becomes gradually thinner moving down from section 3—3. Just above the location of the cross-section 3—3 the stem becomes essentially round, except for anterior and posterior flats 29. The flats 29 extend to a greater or lesser extent along the length of the stem and enhance fixation against rotation about the femoral axis.

In FIG. 1 the neutral axis of bending of the composite structure (the intact bone, hardened cement, and stem) has been drawn in as the line n; the axis n is located near the central axis x of the composite structure. For purposes of the next section of this specification, several parameters of the design are shown in FIG. 3: the radius of $r_0$ of the femur at a given cross-section; radius $r_m$ of the medullary cavity; the radius $r_p$ of the arcuate part of the stem cross-section; the offset distance h from the flat 28 to the center of the circle that forms the arcuate portion of the periphery of the cross-section.

The cross-sectional parameters to be determined for a given bone geometry are $r_p$ and h. The objective in fashioning the best prosthesis is to choose, for each bone diameter, the values of $r_p$ and h that best satisfy the three design criteria, i.e., minimum stem stress in the intact composite structure, minimum stem stress absent proximal support, and minimum decrease in bone stress when the composite structure is intact.

THE METHOD OF DETERMINING STEM PARAMETERS

Stresses due to a bending moment M applied to the composite structure were computed for the case where the circular portion 27 of the prosthesis stem cross-section and the inner and outer surfaces of the bone are concentric. The design stresses were determined using composite beam theory as follows. For the stem as part of the composite, the stress in the prosthesis as part of the composite, $\sigma_{P_{composite}}$ is:

$$\sigma_{P_{composite}} = \frac{M E_P t_P}{E_B I_B + E_C I_C + E_P I_P}.$$

For the stem alone, the stress in the prosthesis, as it would be supporting the load alone, $\sigma_{P_{alone}}$, is:

$$\sigma_{P_{alone}} = \frac{M t_P}{I_P}.$$

For the bone as part of the composite:

$$\sigma_{B_{composite}} = \frac{M E_B t_B}{E_B I_B + E_C I_C + E_P I_P}.$$

And for bone alone:

$$\sigma_{B_{alone}} = \frac{M t_B}{I_B}.$$

The location of the neutral axis of bending of the composite with respect to the centroid of the bone is determined by:

$$\hat{y} = \frac{E_P \bar{y}_P A_P + E_C \bar{y}_C A_C}{E_B A_B + E_C A_C + E_P A_P}.$$

In the above expressions:

$I_B$, $I_C$, $I_P$ are the area moments of inertia of the bone, cement, and prosthesis, respectively;

$E_B$, $E_C$, $E_P$ are the moduli of elasticity of the bone, cement, and prosthesis, respectively;

$A_B$, $A_C$, $A_P$ are the respective areas of the bone, cement, and prosthesis;

$\overline{Y}_p$ and $\overline{Y}_c$ are the location of centroids of the prosthesis and cement with respect to the centroid of the bone; and $t_B$ and $t_p$ are the distances from the neutral axis to the point of maximum stress in the bone and prosthesis, respectively.

The three-criteria design problem can be reformulated as a problem with a single objective and two constraints as follows:

Minimize $\sigma_{Pcomposite}$ subject to:

$\sigma_{Palone} < S_{PF}$, $$\frac{\sigma_{Bcomposite}}{\sigma_{Balone}} > R_{MIN}.$$

Where:

$S_{PF}$ is the fatigue strength of the prosthesis; and $R_{MIN}$ is the minimum allowable ratio of bone stress as part of the composite to bone stress when it alone carries the load.

The value of $S_{PF}$ depends upon the material used and the value of $R_{MIN}$ can be chosen based upon clinical experience and judgment.

THE CHARACTERISTICS OF THE COMPOSITE SYSTEM

The design criteria stresses, $\sigma_{Pcomposite}$, $\sigma_{Palone}$, $\sigma_{Bcomposite}$, and $\sigma_{Balone}$, were computed for a wide range of prosthesis and bone geometries. The procedure for choosing optimum design parameters, $r_p$ and $h$, is demonstrated here for bone geometry that represents a typical large femur. The resulting composite structure is described as follows:

Bone Geometry:
  $r_o = 21.7$ mm
  $r_m = 14.2$ mm

Bending Moment at critical section where stress is greatest:
  $M = 169 \pm 10^3$ N mm (1500 in lb)

Elastic Moduli:
  Bone: $E_B = 17.2 \times 10^3$ MN/m² (2.5 × 10⁶ psi)
  Cement: $E_C = 3.45 \times 10^3$ MN/m² (0.5 × 10⁶ psi)
  Ti 6Al 4V Stem: $E_p = 117 \times 10^3$ MN/m² (17 × 10⁶ psi)
  Co Cr Mo Stem: $E_p = 248 \times 10^3$ MN/m² (36 × 10⁶ psi)

Yield Strength of Ti6Al 4V Stem: $S_Y = 800$ MN/m² (115,000 psi)

Fatigue Strength of Ti 6Al 4V Stem:
  Estimated conservatively to be 0.50 $S_Y$: $S_{PF} = 400$ MN/m² (57,600 psi).

In addition to the above, the minimum allowable ratio, $$R = \frac{\sigma_{Bcomposite}}{\sigma_{Balone}},$$

must be chosen. R values for existing designs were determined using the procedures outlined. It was found that these values consistently fell in the range 0.7 to 0.8. Although the bone is loaded less, no particular long-term problems have been observed to date. Consequently, these stress levels are assumed to be safe, and the minimum value of R was chosen to be:

$R_{MIN} = 0.7$.

Choice of $r_p$

In order to satisfy the second design criterion, a large stem is required. The maximum size must allow a cement layer of sufficient thickness for consistent implantation and good load transfer from the stem to the bone. Structural analyses suggest that cement thickness should be minimized; therefore limitations are based on surgical considerations. Cement thickness will be adequate if the prosthesis radius $r_p$ is no greater than approximately 80% of the cavity radius $r_m$. Therefore, the following values of $r_p$ were used in the design curves presented here.

$r_p = 9.94$ mm ($r_p = 0.7\ r_m$, FIG. 4), $r_p = 11.4$ mm ($r_p = 0.8\ r_m$, FIG. 5).

Choice of Material

Figure 4B:
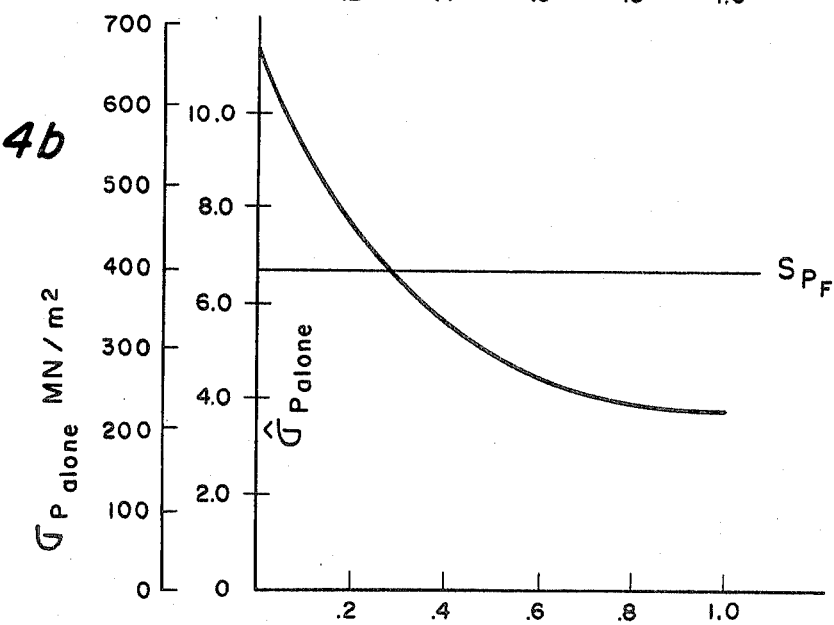
FIG. 4b is a graphical representation of stress in the prosthesis stem alone, plotted against $\tilde{h}$.
Figure 4C:
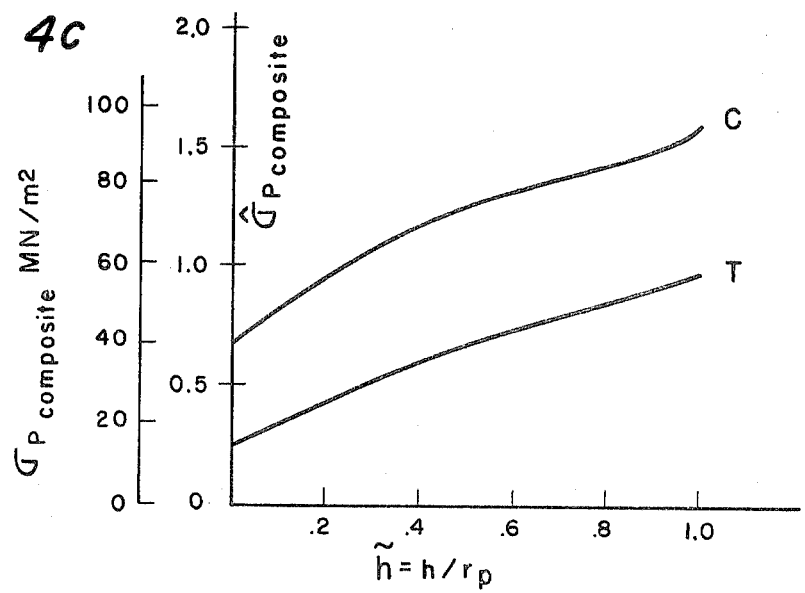
FIG. 4c is a graphical representation of stress in the prosthesis stem in the intact composite structure, plotted against h.
Figure 5A:
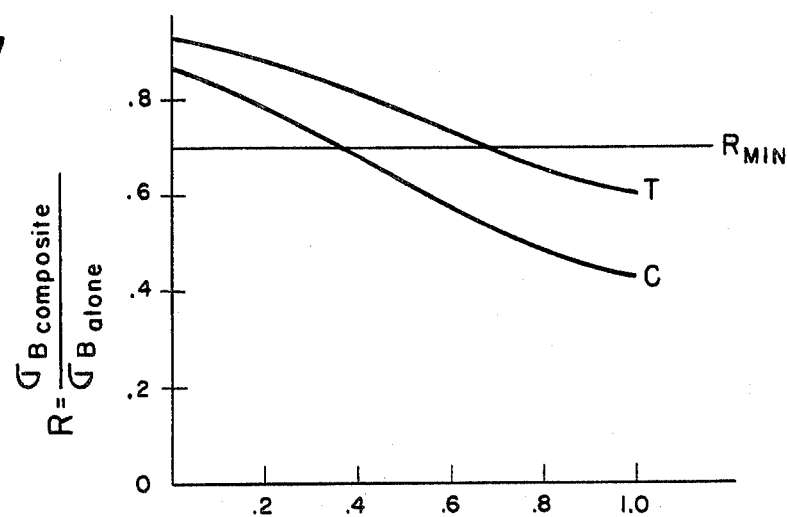
FIG. 5a is a graphical representation similar to that of FIG. 4a, but for a prosthesis stem that is larger in cross-section relative to the medullary cavity.
Figure 5B:
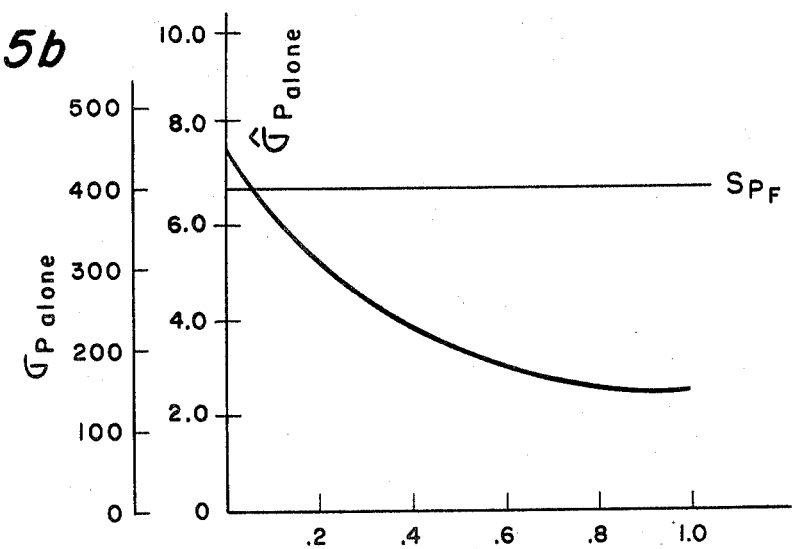
FIG. 5b is a graphical representation like FIG. 4b for the larger prosthesis stem.
Figure 5C:
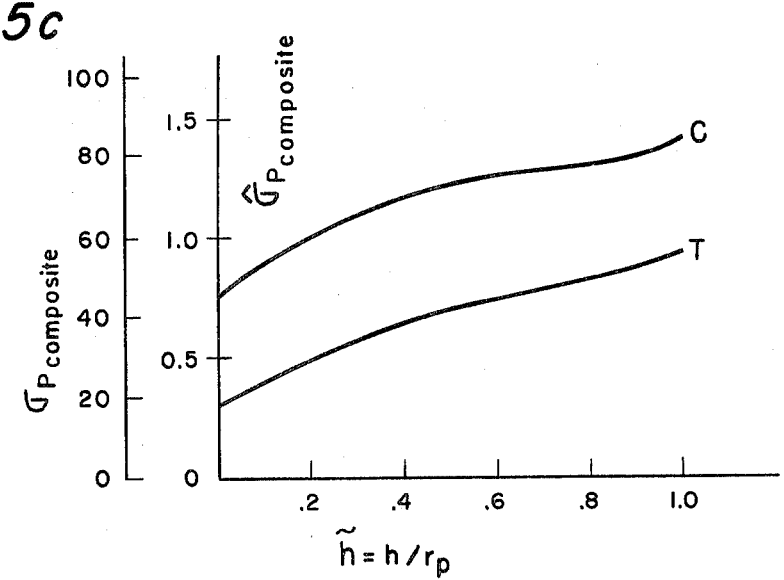
FIG. 5c is a graphical representation like FIG. 4c, but for the larger prosthesis stem.

The choice of stem material was between Ti 6Al 4V (Curve T in FIGS. 4 and 5) and Co Cr Mo (Curve C in FIGS. 4 and 5). Bone stresses, $\sigma_{Bcomposite}$, are always greater (R larger in FIGS. 4a and 5a) for Ti 6Al 4V stems. Prosthesis stem stresses, $\sigma_{Pcomposite}$, are always less for the titanium alloy stems than for the cobalt chrome stems. See FIGS. 4c and 5c. Therefore, the first and third of the foregoing design criteria are satisfied best by Ti 6Al 4V stems. Material choice does not affect satisfaction of the second design criterion, since $\sigma_{Palone}$ is independent of material. See FIGS. 4b and 5b.

Choice of h

It is convenient to determine $\tilde{h}$ as a fraction of $r_p$. Therefore, FIGS. 2 and 3 have been plotted as functions of $\tilde{h} = h/r_p$ For $h = 0$, the cross-sectional shape of the stem is semicircle; for $h = 1$ a circle.

The design constraint that:

$\sigma_{Palone} < S_{PF}$ is only satisfied for values of $\tilde{h}$ greater than approximately 0.5 (FIGS. 4b and 5b).

The design constraint that $$\frac{\sigma_{Bcomposite}}{\sigma_{Balone}} > R_{MIN}$$

is satisfied for all values of $\tilde{h}$ for $r_p = 9.94$ mm ($r_p = 0.7\ r_m$, FIG. 4a) and for values of $\tilde{h}$ less than approximately 0.7 for $r_p = 11.4$ mm ($r_p = 0.8\ r_m$, FIG. 5a).

Therefore, all design criteria are satisfied for values of h between 0.3 and 0.7. Over the range $\sigma_{Palone}$ decreases about 20 percent (FIGS. 4b and 5b), and $\sigma_{Pcomposite}$ increases about 20 percent (FIG. 4c) or 13 percent (FIG. 5c). Since stem stresses, $\sigma_{Pcomposite}$, are well below the fatigue strength of Ti 6Al 4V, the greatest benefit is obtained by taking larger values of $\tilde{h}$ in the acceptable range. Based on this, a value of $\tilde{h} = 0.65$ was chosen.

Although particular characteristics of a preferred embodiment are described above for a typical femur, other hip joint prostheses with stems conforming to both the spirit and the scope of the invention will be readily apparent to those skilled in the art. Accordingly, the foregoing description of a preferred embodiment should not be understood to limit the scope of the invention, which scope is set forth in the appended claims.

We claim:

1. In a femoral component for a hip joint prosthesis adapted to be implanted in a femur and including a ball adapted to replace the head of the femur and a stem adapted to be received in the medullary cavity of the femur and to be affixed therein by a cement, said stem having a proximal portion, an intermediate portion and a distal portion, the improvements wherein each transverse cross section along the intermediate portion of the stem that is subject to the greatest stress is bounded by a generally circular surface of a radius $r_p$ throughout the major portion of the periphery and wherein said circular surface is truncated to provide a flat surface on the lateral side of the stem, as viewed in the lateral-medial plane, thus providing an increased cross-sectional dimension when the stem alone carries the load and affording location of the neutral axis of bending proximate the lateral flat surface in the intact composite structure of stem, cement and bone, wherein the lateral flat surface is spaced apart from the geometric center of the circular surface by a distance h, h being such that $$0.3 \leq h/r_p \leq 0.7,$$

so that the maximum stress within said intermediate portion is less than the fatigue strength of the material of the stem, and wherein the stem is adapted to be received in the medullary cavity such that the flat surface is in close proximity to the neutral axis of bending of the composite bone-cement-prosthesis where tensile stresses due to bending movements are small so that the bone at the lateral side carries a substantial part of the tensile stress of the composite structure and hence bone resorption is inhibited.

2. The component according to claim 1, wherein the distal portion of the stem terminates in a surface inclined downwardly from the lateral to the medial side of the stem and defining means for locating the stem closer the medial side of the medullary cavity as the stem is inserted in a cement filled medullary cavity.

3. The component according to claim 1, wherein the flexibility of said intermediate portion of the stem is such that, $$R = \frac{\sigma_{Bcomposite}}{\sigma_{Balone}} \geq 0.7,$$

where
$\sigma_{Bcomposite}$ is the stress in the bone of the femur proximate the said portion with the stem cemented in place, and
$\sigma_{Balone}$ is the stress in the bone of femur absent said stem and cement and under like load.

4. The component according to claim 1, wherein: $(h/r_p) \approx 0.65$.

5. The component according to claim 1, wherein the material of the stem is Ti 6Al 4V.

6. The component according to claim 1, 3 or 5, wherein the generally rounded portion of the periphery is a portion of a circle having a radius $r_p$ no greater than approximately 80% of the radius $r_m$ of the medullary cavity adjacent a given cross-section of the stem in said portion of greatest stress.

* * * * *